United States Patent
Hammon et al.

(10) Patent No.: US 7,520,964 B2
(45) Date of Patent: Apr. 21, 2009

(54) METHOD FOR THE RECTIFYING SEPARATION OF FLUIDS CONTAINING (METH)ACRYL MONOMERS

(75) Inventors: Ulrich Hammon, Mannheim (DE); Joachim Thiel, Neustadt (DE); Volker Schliephake, Shifferstadt (DE); Juergen Schroeder, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 670 days.

(21) Appl. No.: 10/515,639

(22) PCT Filed: Jul. 2, 2003

(86) PCT No.: PCT/EP03/07026

§ 371 (c)(1),
(2), (4) Date: Dec. 7, 2004

(87) PCT Pub. No.: WO2004/004861

PCT Pub. Date: Jan. 15, 2004

(65) Prior Publication Data

US 2005/0211542 A1    Sep. 29, 2005

(30) Foreign Application Priority Data

Jul. 4, 2002    (DE) .................... 102 30 219

(51) Int. Cl.
*B01D 3/22* (2006.01)
*B01D 3/32* (2006.01)
(52) U.S. Cl. ............... 203/100; 203/DIG. 21; 202/158; 261/128; 261/114.5; 562/600
(58) Field of Classification Search ............ 203/8, 203/9, 100, DIG. 21; 202/158; 261/128, 261/152, 113, 114.5; 562/600
See application file for complete search history.

(56) References Cited

U.S. PATENT DOCUMENTS 3,988,213 A    10/1976    Ohara et al.

(Continued)

FOREIGN PATENT DOCUMENTS

DE    196 06 877    8/1997

(Continued)

OTHER PUBLICATIONS

U.S. Appl. No. 10/515,639, filed Dec. 7, 2004, Hammon et al.

(Continued)

*Primary Examiner*—Virginia Manoharan
(74) *Attorney, Agent, or Firm*—Oblon, Spivak, McClelland, Maier & Neustadt, P.C.

(57) ABSTRACT

A process for rectificatively separating at least one (meth) acrylic monomer-containing fluid by feeding the fluid into a rectification column containing at least one sieve tray without a runoff segment, wherein an elementary cell is obtained from a number of centers of passages in a sieve tray, and the cell shifts regularly and repeatedly along its edges, the lengths of two shifting vectors being the lengths of the edges of the cell along which the shifting is effected;

an arrangement of the centers is such that the positions of an ideal center and a real center are separated by $\leq 1\%$ of half of the sum of the lengths of the two shifting vectors; and an arrangement of the passages is such that the sum of non-overlapping surface areas of an ideal passage with a real passage and vice versa is $\leq 1\%$ of the surface area of the ideal passage.

20 Claims, 5 Drawing Sheets

U.S. PATENT DOCUMENTS

| | | | |
|---|---|---|---|
| 4,208,284 A * | 6/1980 | Pretorius et al. | 210/767 |
| 2004/0116736 A1 | 6/2004 | Machhammer et al. | |
| 2004/0249198 A1 | 12/2004 | Thiel et al. | |
| 2008/0183014 A1 * | 7/2008 | Diefenbacher et al. | 562/600 |

FOREIGN PATENT DOCUMENTS

| | | |
|---|---|---|
| DE | 199 24 532 | 11/2000 |
| DE | 101 15 277 | 6/2002 |
| DE | 101 56 988 | 5/2003 |
| DE | 101 59 823 | 6/2003 |
| DE | 102 18 419 | 6/2003 |
| DE | 102 24 341 | 7/2003 |
| EP | 717 019 | 6/1996 |
| EP | 982 287 | 3/2000 |
| EP | 982 289 | 3/2000 |
| EP | 1 029 573 | 8/2000 |
| EP | 1 125 912 | 8/2001 |
| EP | 1 279 429 | 1/2003 |

OTHER PUBLICATIONS

U.S. Appl. No. 10/494,373, filed May 13, 2004, Hammon et al.
Yung C. Shin "Machine Tools" Handbook of Design, Manufacturing and Automation, John Wiley & Sons. Inc. (pp. 243-258) 1994.
ISO 2768—Teile 1 (Jun. 1991).
DIN 24041 (Oct. 1981).

* cited by examiner

PRIOR ART

PRIOR ART

METHOD FOR THE RECTIFYING SEPARATION OF FLUIDS CONTAINING (METH)ACRYL MONOMERS

The present invention relates to a process for rectificatively separating (meth)acrylic monomer-containing fluids (=the fluid fed to the rectification column) in a rectification column which comprises at least one sieve tray without runoff segment.

The notation (meth)acrylic monomers in this document is an abbreviation of "acrylic monomers and/or methacrylic monomers".

The term acrylic monomers in this document is an abbreviation of "acrolein, acrylic acid and/or esters of acrylic acid".

The term methacrylic monomer in this document is an abbreviation of "methacrolein, methacrylic acid and/or esters of methacrylic acid".

In particular, the (meth)acrylic monomers referred to in this document include the following (meth)acrylic esters: hydroxyethyl acrylate, hydroxyethyl methacrylate, hydroxypropyl acrylate, hydroxypropyl methacrylate, glycidyl acrylate, glycidyl methacrylate, methyl acrylate, methyl methacrylate, n-butyl acrylate, isobutyl acrylate, isobutyl methacrylate, n-butyl methacrylate, tert-butyl acrylate, tert-butyl methacrylate, ethyl acrylate, ethyl methacrylate, 2-ethylhexyl acrylate, 2-ethylhexyl methacrylate, N,N-dimethylaminoethyl acrylate and N,N-dimethylaminoethyl methacrylate.

(Meth)acrylic monomers are important starting compounds for preparing polymers which find use, for example, as adhesives.

(Meth)acrolein and (meth)acrylic acid are prepared on the industrial scale predominantly by catalytic gas phase oxidation of suitable $C_3/C_4$ precursor compounds, in particular of propene and propane in the case of acrolein and acrylic acid, and of isobutene and isobutane in the case of methacrylic acid and methacrolein. However, in addition to propene, propane, isobutene and isobutane, other useful starting materials are other compounds containing 3 or 4 carbon atoms, for example isobutanol, n-propanol or the methyl ether as the $C_4$ precursor of isobutanol. (Meth)acrylic acid may also be obtained from (meth)acrolein.

A product gas mixture is normally obtained from which the (meth)acrylic acid or the (meth)acrolein has to be removed.

This removal is generally carried out in such a manner that the (meth)acrylic acid or (meth)acrolein undergoes initial basic removal by absorption into a solvent (for example water or an organic solvent) or by fractional condensation of the product gas mixture and the resulting condensate or absorbate is subsequently separated rectificatively (in general in more than one stage) to obtain more or less pure (meth)acrylic acid or (meth)acrolein (cf., for example, EP-A 717019, EP-A 1125912, EP-A 982289, EP-A 982287, DE-A 19606877, DE-A 1011527, DE-A 10224341, DE-A 10218419). In this document, the abovementioned fractional condensation shall be regarded as falling under the definition of rectification. It differs from conventional rectification only in that the mixture to be separated is fed to the separating column (the rectification column) in gaseous form (i.e. completely converted to vapor form). The term fluids used in this document shall therefore encompass both liquids and gas mixtures.

Esters of (meth)acrylic acid are obtainable, for example, by direct reaction of (meth)acrylic acid and/or (meth)acrolein with the appropriate alcohols. However, product mixtures also occur in this case from which the (meth)acrylic ester has to be removed, for example rectificatively.

The abovementioned (meth)acrylic monomer-containing fluids or liquids may comprise the (meth)acrylic monomers either in more or less pure form or in solution.

The solvent may either be aqueous or an organic solvent. The specific type of the solvent is substantially insignificant to the invention. The content of (meth)acrylic monomers may be $\geq$2% by weight, $\geq$5% by weight, or $\geq$10% by weight, or $\geq$20% by weight, or $\geq$40% by weight, or $\geq$60% by weight, or $\geq$80% by weight, or $\geq$90% by weight, or $\geq$95% by weight, or $\geq$99% by weight.

Depending on their composition, the fluids or liquids comprising the (meth)acrylic monomers described can be rectificatively separated either in such a manner that the (meth)acrylic monomers accumulate at the top of the rectification column or in such a manner that the (meth)acrylic monomers accumulate in the bottom of the rectification column. It will be appreciated that the (meth)acrylic monomer-enriched fractions may be also withdrawn in the upper, lower or middle section of the rectification column.

In all cases (in particular the abovementioned), rectification columns which comprise at least one sieve tray without runoff segment (cf. for example, DE-A 19924532) may be used for the rectificative separation in question. However, it will be appreciated that these rectification columns may also comprise exclusively sieve trays without runoff segments as the sole separating internals of the rectification column (cf., for example, DE-A 10156988 and EP-A 1029573). It is also possible to use other separating internals, for example bubble cap trays or structured packings.

The rectification may be carried out either under atmospheric pressure or under reduced pressure. Typical bottom temperatures are in the range from 100 to 250° C. and typical top pressures are from 80 to 500 mbar.

The solvents frequently accompanying the (meth)acrylic monomers often comprise diphenyl, for example mixtures of diphenyl ether, diphenyl and o-dimethyl phthalate. An example of a solvent which is frequently used for the absorption of (meth)acrylic monomers comprises about 57.4% by weight of diphenyl ether, 20.7% by weight of diphenyl and 20% by weight of o-dimethyl phthalate. Other solvents frequently accompanying (meth)acrylic acid and (meth)acrylic esters are methyl acrylate and ethyl acrylate.

In general, the rectification column in the rectifications discussed in this document is polymerization-inhibited using polymerization inhibitors. These are customarily introduced in the top of the column, but may in addition also be added to the liquid phase and also already have been added to the liquid to be separated which comprises the (meth)acrylic monomers. Typical representatives of such polymerization inhibitors include phenothiazine, 2-methoxyphenol and 4-hydroxy-2,2,6,6-tetramethylpiperidine N-oxyl. Based on the content of (meth)acrylic monomers, up to a few hundred ppm by weight of polymerization inhibitors are frequently used.

Now that the (meth)acrylic monomer-containing fluids and liquids which are particularly relevant to this document have been described in detail above, the sieve trays without runoff segments shall now be considered in detail. In the literature, the term dual-flow trays is also frequently used for such trays. In this document, this term is considered to refer to plates having simple passages (holes, slits, etc.) which in many cases are also referred to as trickle sieve trays.

The absence of runoff segments (runoff shafts) causes the rising gas and the reflux liquid falling in the column to flow in opposite directions through the same passages of the tray. The cross section of the passages is adjusted in a manner known per se to the loading of the column. Where it is too small, the rising gas flows through the passages at such high speed that the reflux liquid falling in the column is entrained substantially without separation. When the cross section of the passages is too large, rising gas and falling reflux move past each other substantially without exchange and the tray is at the risk of running dry. In other words, the working range for dual flow trays is defined by 2 limiting points. There has to be a minimum limiting speed, so that a certain liquid layer is maintained on the tray in order to allow the tray to work. The upper limit is defined by the flood point when the speed leads to liquid build-up on the tray and prevents trickle through. In the normal working range, the liquid refluxing in the rectification column trickles in drops from dual-flow tray to dual-flow tray, i.e. between the trays, the continuous gas phase is interspersed by a divided liquid phase. Some of the drops striking the trickle sieve tray are atomized.

In general, each dual-flow tray is connected flush to the column walls. However, there are also embodiments in which there is an intermediate space between column wall and tray which is only partially interrupted by bridges. In addition to the actual passages, it may, if need be, have further orifices which facilitate, for example, securing of the tray to support rings or the like (cf., for example, DE-A 10159823).

For rectificative treatment of (meth)acrylic monomer-containing liquids, the earlier application DE-A 10156988 recommends rectification columns having dual-flow trays having passages whose cross section, although constant within one dual-flow tray, decreases with increasing separation of the tray from the feed of the liquid to be treated.

According to the teaching of DE-A 10156988, the longest extent of the passages is typically from 10 to 80 mm. However, a disadvantage of the teaching of DE-A 10156988 is that it makes no statements as to how the passages within one dual-flow tray should be arranged relative to one another. The same applies to the teaching of EP-A 1029573. In both documents, recommendation is merely made of circular drillholes as preferred passages.

However, intensive in-house investigations have shown that the relative arrangement of the passage of a dual-flow tray has a decisive influence on the separating performance of the tray in the rectificative separation of (meth)acrylic monomer-containing fluids or liquids. This is true in particular when the (meth)acrylate monomer content of the fluid or of the liquid is from 2 to 5% by weight, or from 10 to 35% by weight, or $\geq 95\%$ by weight.

In this context, it was also found that the irregular triangular pitch (the location of the centers of the drillholes deviates distinctly from a location on theoretical straight lines) graphically represented in FIG. 1 of EP-A 1029573 as a possible relative arrangement is not completely satisfactory.

Figure 1:
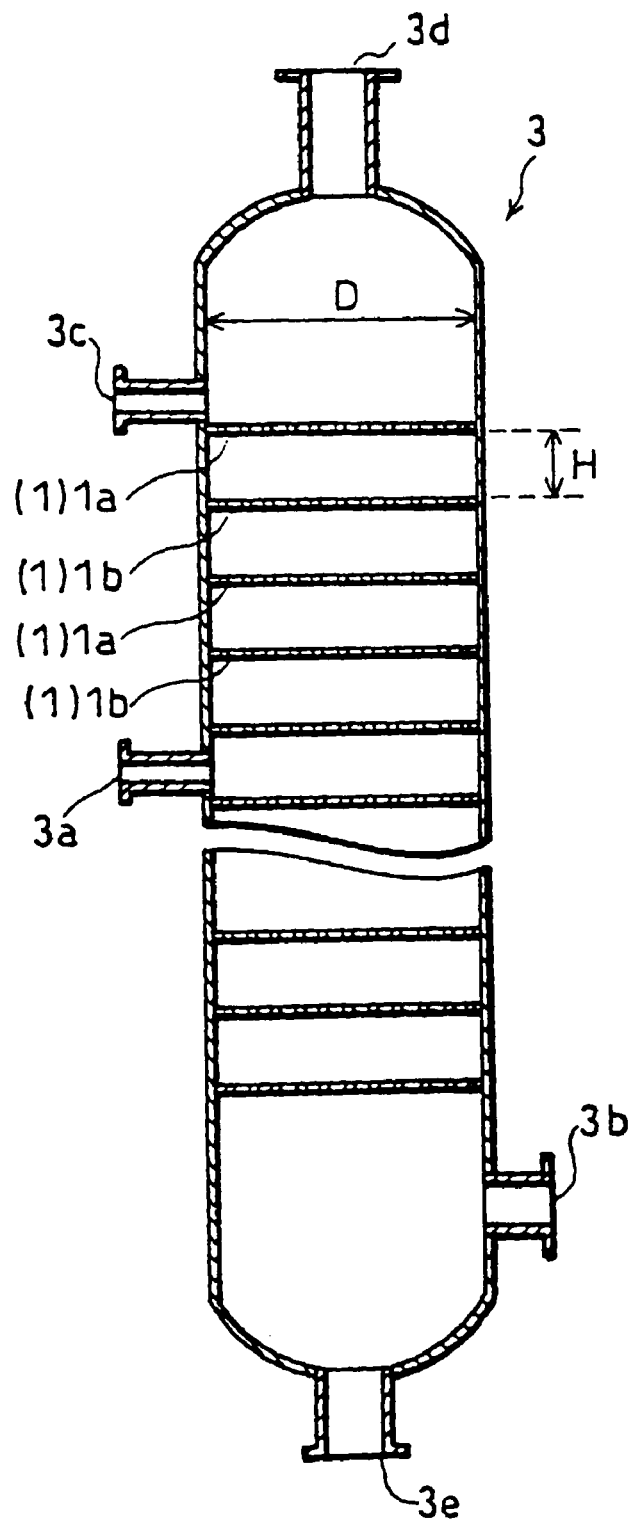
FIG. 1 is a copy of FIG. 3 of EP1029573 illustrating a column (3) comprising sieve trays (1).

It is an object of the present invention to provide an improved relative arrangement of the passages of the trickle sieve tray for the rectificative separation of (meth)acrylic monomer-containing fluids (in particular the abovementioned fluids) in a rectification column which has at least one sieve tray without runoff segment to the effect that the trickle sieve tray has an improved separating performance.

We have found that this object is achieved by a process for rectificatively separating (meth)acrylic monomer-containing fluids in a rectification column which comprises at least one sieve tray without a runoff segment, wherein both the arrangement of the centers of the passages present in the sieve tray and the arrangement of the passages themselves are regular and can be obtained from a basic number of these centers and passages by defining a rectangular elementary cell in the sieve tray which contains the basic number and has four edges, of which two in each case are parallel to one another and of equal length, and this elementary cell shifts regularly and repeatedly along its edges, the length of the shifting vector in each case being the length of the edge of the elementary cell along which the shifting is effected.

According to the invention, two edges of the elementary cell are regarded as parallel to one another when the angle formed by their directions is $\leq 0.2°$. The abovementioned angle is preferably less than 10 angle minutes, more preferably less than 5 angle minutes and most preferably less than 2 angle minutes. At best, this angle is 0°.

According to the invention, two parallel edges of the elementary cell are in a similar manner regarded as being equally long when the difference in length, based on half of the sum of their lengths, is $\leq 1\%$, preferably $\leq 0.5\%$, more preferably $\leq 0.25\%$, and most preferably $\leq 0.1\%$. At best, the lengths are identical. When the lengths are not equal, the length of the shifting vector according to the claim is equal to half of the sum of the lengths. Normally, the elementary cell will not contain more than ten centers of passages. Usually, it contains $\leq 8$, frequently $\leq 5$ or $\leq 4$, centers of passages.

Normally, this number of centers of an elementary cell is $\leq 10\%$, usually $\leq 7\%$, in many cases $\leq 5\%$ and frequently $\leq 3\%$ of all the centers of passages contained in the trickle sieve tray.

The center of a passage refers to the theoretical center of mass which results when the passage is filled with a homogeneous mass which has the same filling thickness at each point in the orifice.

In principle, the passages of the at least one trickle sieve tray to be used according to the invention may have any geometric shape. In other words, the passages may be circles, ellipses, rectangles, triangles, polygons or slits.

According to the invention, all passages of an at least one trickle sieve tray to be used according to the invention advantageously have the same geometric shape and the same cross section. In this case, the difference between the largest and the smallest cross section of the passages captured by the elementary cell is preferably $\leq 1\%$, better $\leq 0.75\%$, better still $\leq 0.5\%$, better still $\leq 0.25\%$, better still $\leq 0.1\%$ and at best 0%, based on the surface area of the largest cross section captured. This geometric shape is preferably circular. However, it will be appreciated that there may also be passages of different geometric shape and different cross section within the elementary cells relevant to the invention.

The regular arrangement of the centers required according to the invention should be regarded as fulfilled when the regularly repeating shifting of the elementary cell along its edges results, in at least 90% (preferably at least 95%, more preferably at least 98%, even more preferably at least 99% or 99.9% and at best 100%) of all cases, in the position of the ideal image of the center generated by the shifting and the position of the corresponding real center present in the sieve tray being separated by $\leq 1\%$, preferably $\leq 0.75\%$, more preferably by $\leq 0.5\%$, even more preferably by $\leq 0.3\%$ and even better by $\leq 0.1\%$, of half of the sum of the lengths of the two possible shifting vectors. In general, this separation between ideal and real center in the appropriate number of cases will be $\leq 0.1$ mm, preferably $\leq 0.05$ mm and more preferably $\leq 0.02$ mm. Ideally, ideal and real centers coincide in all cases.

The regular arrangement of the passages required according to the invention should be regarded as fulfilled when, on the one hand, the abovementioned regular arrangement of the centers is fulfilled in each case (i.e. the abovementioned condition in each case is fulfilled) and, on the other hand, the regularly repeating shifting of the elementary cell along its edges results in at least 90% (preferably at least 95%, more preferably at least 98%, even more preferably at least 99% or 99.9% and at best 100%) of all cases in the surface area of the ideal passage generated by the shifting and the surface area of the associated real passage present in the sieve tray overlapping with each other to such an extent that the sum of the nonoverlapping residual surface area of the ideal passage generated by the shifting and the nonoverlapping residual surface area of the corresponding real passage, based on the surface area of the ideal passage generated by the shifting, (referred to hereinbelow as $S_{Rem.}$) is $\leq 1\%$, preferably $\leq 0.75\%$, more preferably $\leq 0.5\%$, even more preferably $\leq 0.3\%$ and even better $\leq 0.1\%$. Ideally, $S_{Rem.}=0$.

Figure 3:
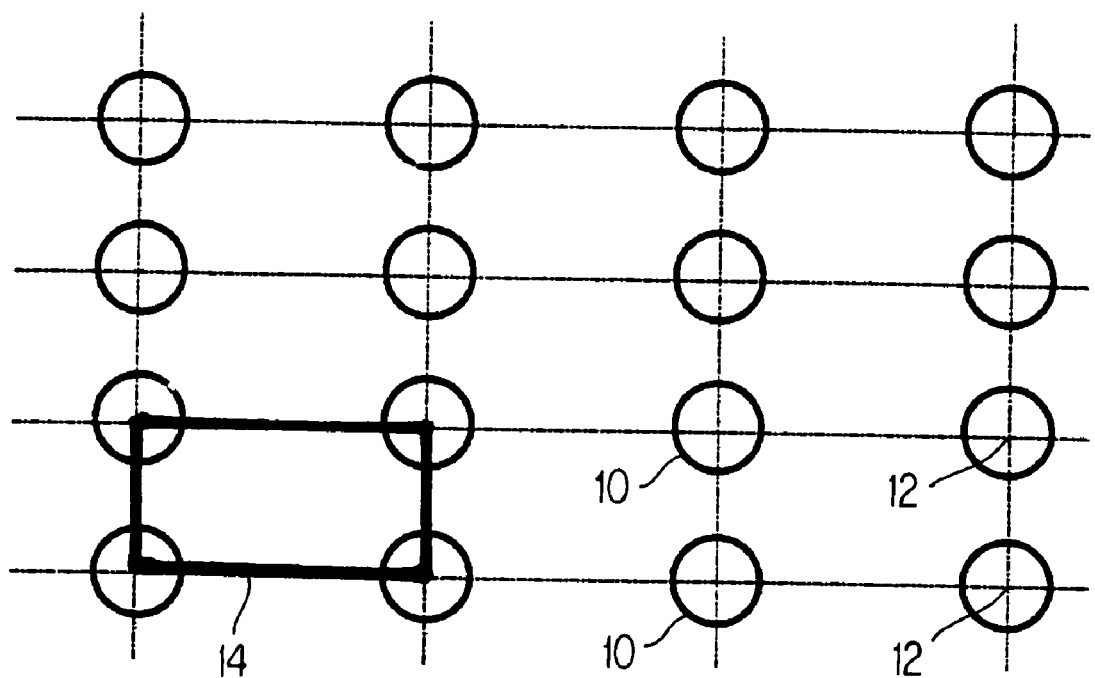
FIGS. 3-7 each illustrate a configuration of sieve tray passages (10) of the present invention, centers (12) of the passages (10), and an elementary cell (14) obtained from a number of centers (12).
Figure 4:
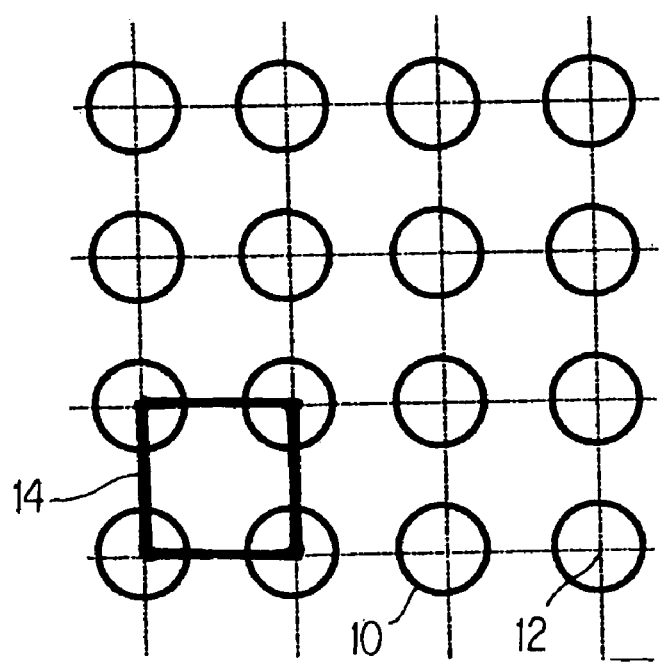
Figure 5:
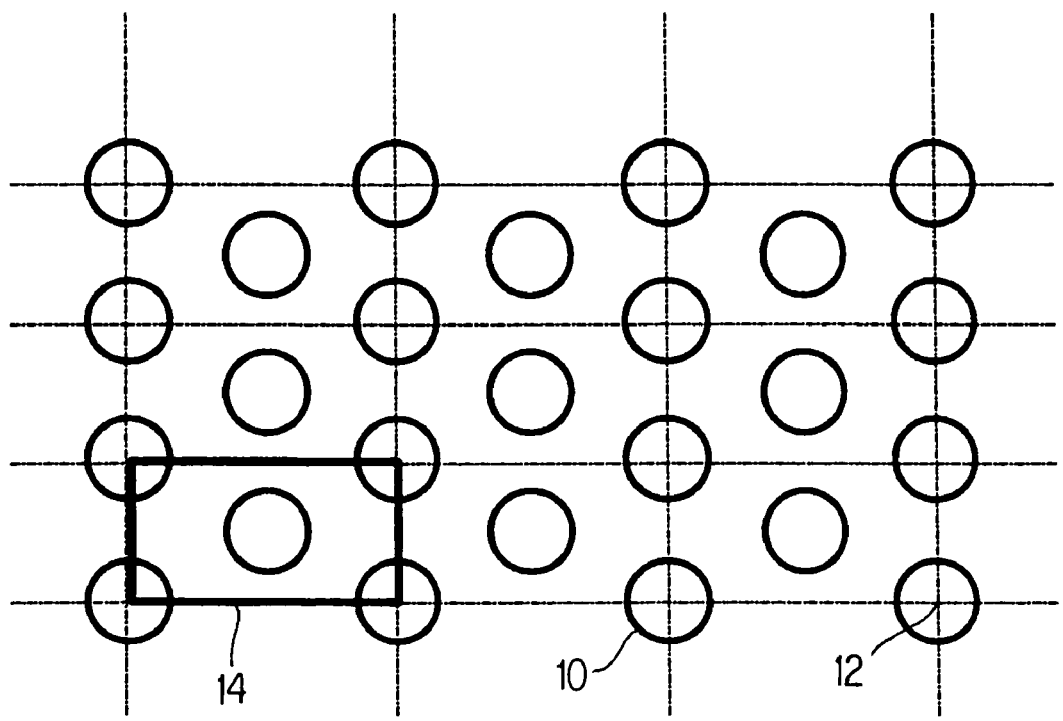
Figure 6:
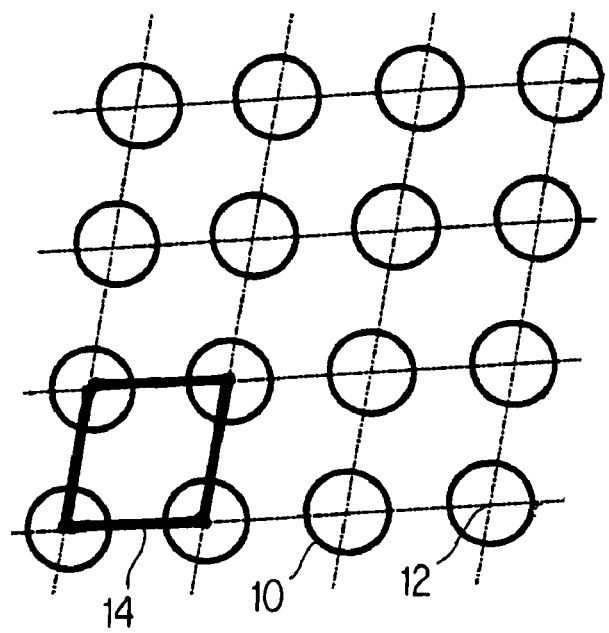
Figure 7:
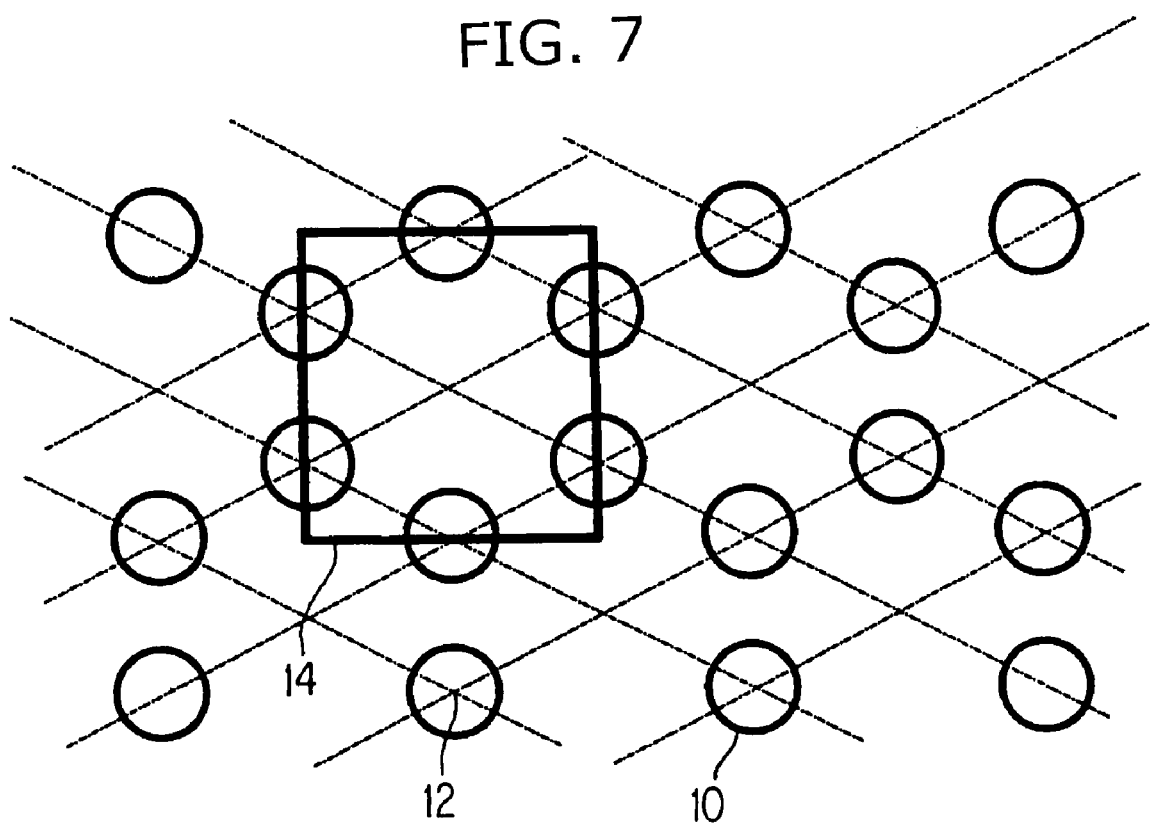

Elementary cells advantageous according to the invention have the geometry of a rectangle (cf. FIG. 3, 5 (rectangular face-centered elementary cell) and 7), of a square (cf. FIG. 4) or of a rhombus (cf. FIG. 6). This is also the case when the relationship $d = a \cdot \sqrt{3}$ in FIG. 5 between the longer edge d and the shorter edge a is not fulfilled or the edges in FIG. 6 are not at equal length and/or the angle between them is not 60°. Particular preference is given to an arrangement of the passages in which the elementary cell is a face-centered square (i.e. corresponding to FIG. 5 with four identical edge lengths).

Otherwise, the at least one trickle sieve tray without runoff segment to be used may be configured and arranged in the column as described in DE-A 10156988 or in EP-A 1029573.

Processes according to the invention are therefore those in which rectification columns are used which, as separating internals, have trays of whose number at least one, preferably more than one (preferably $\geq 10\%$, or $\geq 20\%$, or $\geq 30\%$, or $\geq 40\%$, or $\geq 50\%$, or $\geq 60\%$, or $\geq 75\%$, of all trays) and more preferably all are trickle sieve trays according to the invention, of which trickle sieve trays having circular passages are preferred. It is advantageous when, in addition, all circular orifices within one trickle sieve tray have the same cross section.

Preference is given according to the invention to processes in rectification columns whose separating internals are exclusively trickle sieve trays of the type to be used according to the invention. This is true in particular when the passages are circular, and in particular when the hole diameter is varied from tray to tray according to DE-A 10156988. However, they may also be constant over all trays. The thickness of the at least one trickle sieve tray to be used in the process according to the invention is advantageously from 2 mm to 12 mm.

According to the invention, the orifice ratio (ratio of the total surface area of all passages of the at least one trickle sieve tray to be used according to the invention to the total surface area of this trickle sieve tray) is generally advantageously from 0.1 to 0.3.

The separation T between two neighboring centers in an at least one trickle sieve tray to be used according to the invention is customarily 1.2 d to 3 d, where d is the length of the longest extent of the larger passage (in the case of a circle the circle diameter). d is typically from 10 to 80 mm, frequently from 10 to 25 mm.

When the rectification column used in the process according to the invention has two or more successive trickle sieve trays to be used according to the invention, the separation is advantageously from 0.1 D to 0.5 D, where D is the diameter of the trays or the internal diameter of the rectification column.

The trickle sieve trays to be used according to the invention are preferably manufactured from stainless steel, in particular stainless steel 1.4571 (according to DIN EN 10020).

Finally, it is once again emphasized that the result of the present invention is that trickle sieve trays having strictly regular arrangements of the passages are superior to trickle sieve trays having irregular arrangement of the passages with regard to the rectificative separation performance of (meth) acrylic monomer-containing fluids or liquids. It will be appreciated that the rectification columns to be used according to the invention may also be used for other thermal separating processes, for example extractions or strippings, or for rectificative separations of other fluids or liquids.

Trickle sieve trays to be used according to the invention are notable for low tendency to polymer formation.

It is self-evident that it is possible in the peripheral area of the at least one sieve tray without runoff segment only to apply part of the elementary cell to the passages present there.

The process according to the invention is suitable in particular for the processes of fractional condensation or rectification described in DE-A 19924532, DE-A 10115277, EP-A 982289, EP-A 982287 and EP-A 982288.

EXAMPLES

The Tray Numbering Rises Within the Column From the Bottom to the Top

Example 1

120 t per hour of a mixture of 67% by weight of Diphyl® (mixture of about 25% by weight of diphenyl and about 75% by weight of diphenyl ether), 16% by weight of dimethyl phthalate, 15.8% by weight of acrylic acid, 300 ppm by weight of phenothiazine and the remainder of small amounts of compounds such as benzaldehyde, acetic acid, propionic acid, furfurals, formic acid and formaldehyde was fed to a tray column which had 40 equidistant (40 cm) dual-flow trays. The rectification column was operated at a reflux ratio of 2.2. The column bottom was heated with a forced-circulation evaporator and the vapors were condensed with an injection condenser which injected reflux cooled to a temperature of 45° C. The bottom temperature was 214° C., the top pressure 225 mbar. The mixture was fed to the 10th tray. At tray 32, the removed acrylic acid was withdrawn. For experimental purposes, trays 30, 31 and 32 were exchangeable; below tray 30 30 (at tray 29) and immediately above tray 32, a sample withdrawal device was installed which allowed a sample to be withdrawn from the appropriate liquid phase. Above the 40th tray, a liquid distributor was installed which distributed about 60 t per hour of reflux, stabilized with 280 ppm by weight of phenothiazine, into the rectification column having a diameter of 3.50 m. The distributor consisted of three cubic boxes arranged in parallel and open at the top which have a length of 3 m, a width of 20 cm and a height of 25 cm. The upper end of each box was configured as a toothed weir.

After a running time of 10 days, samples were taken at the abovementioned sampling points. The withdrawn acrylic acids had the compositions listed in Table 1.

The relative arrangement of the passages in trickle sieve trays 30 to 32 was as follows:

- elementary cell: ideally as in FIG. 5 where $d=a\cdot\sqrt{3}$ and d is the longer and a the shorter edge of the elementary cell, d=58.88 mm;
- the elementary cell contained five centers of passages, four of them on the corners of the elementary cell;
- the passages were all circular and had a uniform target diameter of 15 mm which was fulfilled in all cases within a range of variation of ±0.01 mm;
- the separation between two neighboring centers within the elementary cell was 34 mm;
- the orifice ratio was 0.16;
- the regularly repeating shifting of the elementary cell along its edges resulted in 99.6% of all cases in the position of the image of the ideal center generated by the shifting and the position of the corresponding real center present in the sieve tray being separated from one another by ≦0.1% of the length of half of the shifting vector sum;
- regularly repeating shifting of the elementary cell along its edges resulted in 99.8% of all cases in $S_{Rem.}$ ≦0.1%.

TABLE 1

|  | Below tray 30 | Above tray 32 |
|---|---|---|
| Acrylic acid | 99.12% by weight | 99.58% by weight |

Comparative Example

Figure 2:
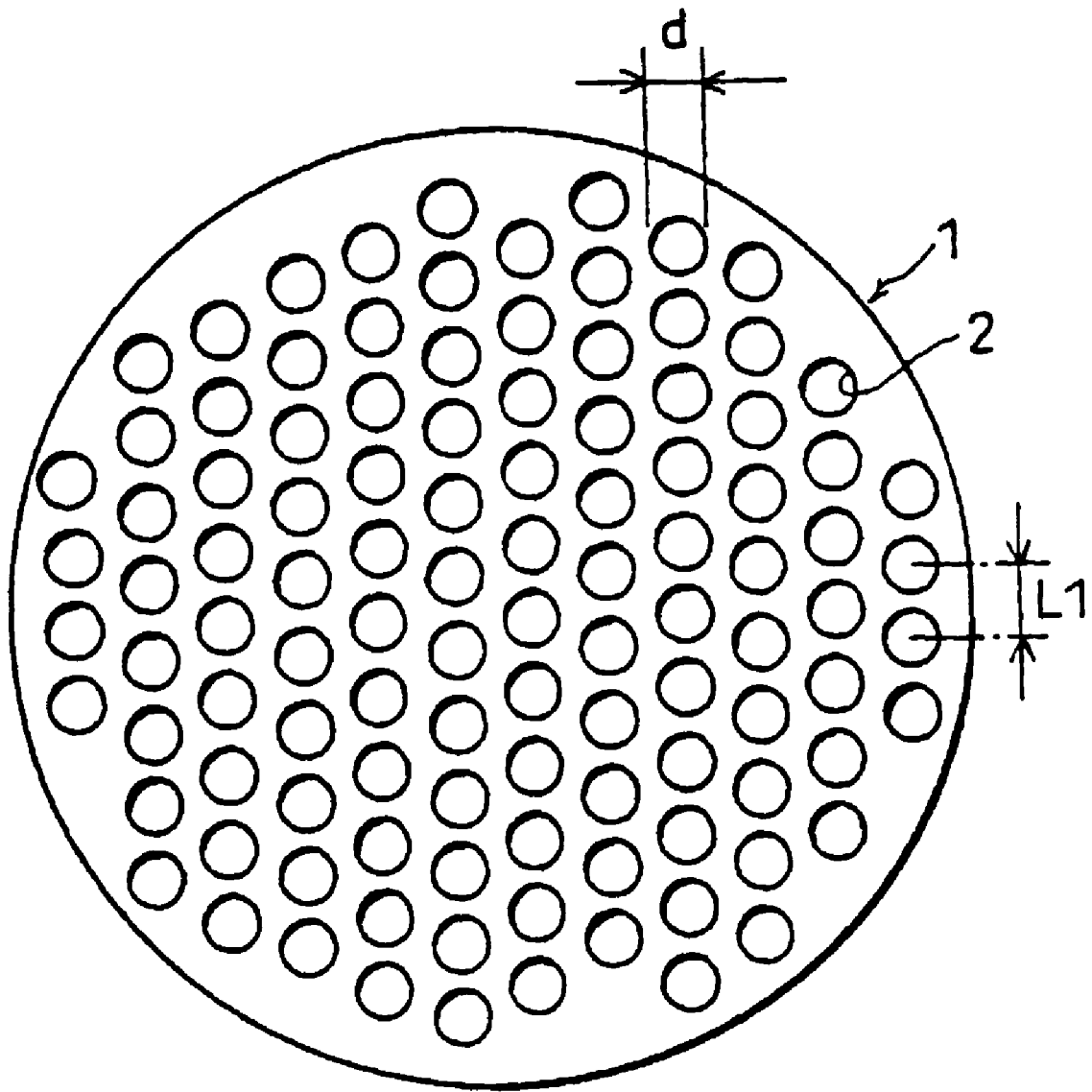
FIG. 2 is a copy of FIG. 1 of EP1029573 illustrating a sieve tray (1) and holes (2).

As in Example 1, except that trays 30, 31 and 32 were replaced by trays according to FIG. 1 of EP-A 1029573. FIG. 2 of this document, which is an original copy of the abovementioned FIG. 1 assumes the deviations from the ideal line.

In all three exchanged trays, the prerequisites of the trays from Example 1 were fulfilled with from the following two exceptions:

- regularly repeating shifting of the elementary cell along its edges resulted only in 89% of all cases in the position of the image of the ideal center generated by the shifting and the position of the corresponding real center present in the sieve tray being separated by ≦1% of the length of half of the shifting vector sum;
- regularly repeating shifting of the elementary cell along its edges resulted only in 86% of all cases in $S_{Rem.}$≦1%.

After a running time of 10 days, samples were taken as in Example 1. The analysis results are:

TABLE 2

|  | Below tray 30 | Above tray 32 |
|---|---|---|
| Acrylic acid | 99.13% by weight | 99.39% by weight |

Example 2

As in Example 1. Everything was identical, except that the elementary cell of trays 30 to 32 was a face-centered square (as in FIG. 5, except a =d=45 mm).

After a running time of 10 days, samples were taken as in Example 1. The analysis results are:

TABLE 3

|  | Below tray 30 | Above tray 32 |
|---|---|---|
| Acrylic acid | 99.09% by weight | 99.59% by weight |

Example 3

As in Example 1. Everything was identical, except that the elementary cell of trays 30 to 32 was rectangular as in FIG. 3. The edge lengths were 28 mm and 35 mm.

After a running time of 10 days, samples were taken as in Example 1.

The analysis results are:

TABLE 4

|  | Below tray 30 | Above tray 32 |
|---|---|---|
| Acrylic acid | 99.15% by weight | 99.52% by weight |

The experiments carried out resulted in the following order of effectiveness:

Example 2>Example 1>Example 3>Comparative Example.

We claim:

1. A process for rectificatively separating at least one (meth)acrylic monomer-containing fluid, comprising
   feeding the at least one (meth)acrylic monomer-containing fluid into a rectification column which comprises at least one sieve tray without a runoff segment, wherein
   an elementary cell, of parallelogram shape, is obtained from a number of centers of passages present in the at least one sieve tray, and the elementary cell shifts regularly and repeatedly along its edges, the length of each of two shifting vectors being the length of the edge of the elementary cell along which the shifting is effected;
   an arrangement of the centers of passages of the at least one sieve tray, in at least 90% of all cases, is such that the position of an ideal center and the position of a corresponding real center are separated by ≦1% of half of the sum of the lengths of the two shifting vectors; and
   an arrangement of the passages, as a whole, of the at least one sieve tray, in at least 90% of all cases, is such that the sum of non-overlapping surface area of an ideal passage with a corresponding real passage and non-overlapping surface area of the corresponding real passage with the ideal passage is ≦1% of the surface area of the ideal passage ($S_{Rem}$).

2. The process as claimed in claim 1, wherein the passages are circular.

3. The process as claimed in claim 2, wherein the (meth) acrylic monomer of the at least one (meth)acrylic monomer-containing fluid is acrylic acid.

4. The process as claimed in claim 2, wherein the at least one (meth)acrylic monomer-containing fluid comprises diphenyl as solvent.

5. The process as claimed in claim 1, wherein the rectification column comprises more than one sieve tray, and wherein the only separating internals of the rectification column are sieve trays without a runoff segment, as defined in claim 1.

6. The process as claimed in claim 5, wherein the (meth) acrylic monomer of the at least one (meth)acrylic monomer-containing fluid is acrylic acid.

7. The process as claimed in claim 5, wherein the at least one (meth)acrylic monomer-containing fluid comprises diphenyl as solvent.

8. The process as claimed in claim 5, wherein the passages in the at least one sieve tray are circular.

9. The process as claimed in claim 8, wherein the (meth) acrylic monomer of the at least one (meth)acrylic monomer-containing fluid is acrylic acid.

10. The process as claimed in claim 8, wherein the at least one (meth)acrylic monomer-containing fluid comprises diphenyl as solvent.

11. The process as claimed in claim 1, wherein the (meth) acrylic monomer of the at least one (meth)acrylic monomer-containing fluid is acrylic acid.

12. The process as claimed in claim 11, wherein the at least one (meth)acrylic monomer-containing fluid comprises diphenyl as solvent.

13. The process as claimed in claim 11, wherein the acrylic acid content of the at least one (meth)acrylic monomer-containing fluid is from 2 to 5% by weight, from 10 to 35% by weight, or $\geqq 95\%$ by weight.

14. The process as claimed in claim 13, wherein the at least one (meth)acrylic monomer-containing fluid comprises diphenyl as solvent.

15. The process as claimed in claim 1, wherein the at least one (meth)acrylic monomer-containing fluid comprises diphenyl as solvent.

16. The process as claimed in claim 1, wherein the elementary cell is a face-centered square.

17. The process as claimed in claim 1, wherein the elementary cell is a rectangle.

18. The process as claimed in claim 1, wherein the elementary cell is a rhombus.

19. The process as claimed in claim 1, wherein the at least one (meth)acrylic monomer-containing fluid is a liquid.

20. The process as claimed in claim 1, wherein the at least one (meth)acrylic monomer-containing fluid is a gas mixture.

* * * * *